United States Patent
Rossier et al.

(10) Patent No.: US 7,098,450 B2
(45) Date of Patent: Aug. 29, 2006

(54) APPARATUS AND METHOD FOR DISPENSING A SAMPLE

(75) Inventors: Joel Stephane Rossier, Saillon (CH); Frédéric Reymond, La Conversion (CH); Hubert Hugues Girault, Ropraz (CH); Tatiana Rohner, Renens (CH); Niels Lion, Lausanne (CH); Véronique Gobry, Chavannes-Près-Renens (CH)

(73) Assignees: Ecole Polytechnique Federale de Lausanne, (CH); DiagnoSwiss S.A., (CH)

( * ) Notice: Subject to any disclaimer, the term of this patent is extended or adjusted under 35 U.S.C. 154(b) by 0 days.

(21) Appl. No.: 10/467,973

(22) PCT Filed: Feb. 13, 2002

(86) PCT No.: PCT/EP02/01998

§ 371 (c)(1),
(2), (4) Date: Aug. 13, 2003

(87) PCT Pub. No.: WO02/080222

PCT Pub. Date: Oct. 10, 2002

(65) Prior Publication Data

US 2004/0075050 A1   Apr. 22, 2004

(30) Foreign Application Priority Data

Feb. 13, 2001   (GB) ................. 0103516.1

(51) Int. Cl.
*B01D 59/44* (2006.01)
*H01J 49/00* (2006.01)

(52) U.S. Cl. ..................... 250/288; 250/281

(58) Field of Classification Search ........... 250/281, 250/282, 288; 204/451, 601; 205/792; 427/488
See application file for complete search history.

(56) References Cited

U.S. PATENT DOCUMENTS

| | | | |
|---|---|---|---|
| 5,872,010 A | 2/1999 | Karger et al. | 436/173 |
| 5,994,696 A | 11/1999 | Tai et al. | 250/288 |
| 6,110,343 A * | 8/2000 | Ramsey et al. | 204/601 |
| 6,175,112 B1 * | 1/2001 | Karger et al. | 250/288 |
| 6,228,434 B1 * | 5/2001 | Affinito | 427/488 |
| 6,231,737 B1 * | 5/2001 | Ramsey et al. | 204/451 |
| 6,558,902 B1 * | 5/2003 | Hillenkamp | 435/6 |
| 6,579,452 B1 | 6/2003 | Moon et al. | 210/198.2 |
| 6,699,384 B1 * | 3/2004 | Lin et al. | 205/792 |

(Continued)

FOREIGN PATENT DOCUMENTS

WO   WO 98/35226   8/1998

(Continued)

OTHER PUBLICATIONS

Rohner et al., "Polymer Microspray with an Integrated Thick-Film Microelectrode", Analytical Chemistry, vol. 73, No. 22, pp. 5353-5357, Nov. 2001.

(Continued)

*Primary Examiner*—Frank G. Font
*Assistant Examiner*—Mary El-Shammaa
(74) *Attorney, Agent, or Firm*—Howson and Howson (57) ABSTRACT

The present invention relates to an apparatus and a method of fabricating the apparatus for dispensing a sample for subsequent analysis by mass spectrometry. The apparatus comprises a polymer substrate (1), in which a covered microchannel (3) has been etched, a wall of the microchannel comprising an electrically conductive material (2) for applying a voltage allowing the sample to be sprayed into a mass spectrometer from the open end (4) of the microchannel. The present application also discloses various applications of the apparatus.

29 Claims, 12 Drawing Sheets

U.S. PATENT DOCUMENTS

2002/0079219 A1    6/2002    Zhao et al. .................. 204/451
2004/0043479 A1*   3/2004    Briscoe et al. ........... 435/288.5

FOREIGN PATENT DOCUMENTS

| WO | WO 98/35376 | 8/1998 |
| WO | WO 00/15321 | 3/2000 |
| WO | WO 02/24322 | 3/2002 |

OTHER PUBLICATIONS

Valaskovic et al., "Long-Lived Metallized Tips for Nanoliter Electrospray Mass Spectrometry", Journal of American Society for Mass Spectrometry, vol. 7, pp. 1270-1272, Aug. 1996.

Kriger et al., "Durable Gold-Coated Fused Silica Capillaries for Use in Electrospray Mass Spectrometry", Analytical Chemistry, vol. 67, No. 2, Jan. 1995.

* cited by examiner

APPARATUS AND METHOD FOR DISPENSING A SAMPLE

BACKGROUND TO THE INVENTION

The present invention relates to apparatus for dispensing a sample for subsequent analysis by mass spectrometry, and to a method of fabricating such apparatus.

Mass spectrometry is a performant analytical technique, which provides information about the chemical nature of analyzed molecules. The application domain of mass spectrometry analysis has grown in the past few years with the development of technologies which allow the injection of a broad range of molecules. Among the different feeding processes, the electrospray or nanospray is a method of choice, where the sample is diluted in a solvent and sprayed from a flow of solution under a high voltage ionization.

Recent developments have allowed the automation of the feeding of samples to a mass spectrometer (MS) in order to enhance the throughput of the analysis. Indeed, mass spectrometry analysis is a rapid technique that can work with a scan rate of more that 10 kHz. On the other hand, more and more performant informatic tools allow the rapid treatment of data for example with new software that is able to compare the obtained data with a full database in a very short time. Therefore, the need for fast and automated sampling systems is growing.

Different designs have been presented for fabricating a nanospray. The more common way is to pull a capillary and to metallize its external surface. The capillary is then connected to a nanospray tip and placed in front of a mass spectrometer. This method is convenient but difficult to fabricate in a reproducible way. Such a system is however easier to fabricate in a planar microchip, also called a microfluidic device as used in the present invention.

A standard electrospray is composed of a capillary end that is surrounded by a metallic substrate to apply the high voltage, while sheath liquid and sheath flow are provided to enhance the performances of the ionization and evaporation of the solvent. More recently, various approaches have been investigated to provide sheathless electrospray systems where a capillary with small enough dimensions insures an efficient spray (see Wahl J H et al, Electrophoresis, 1993, vol. 14, p 448). Alternatively, WO 98/35226 describes inserting a platinum wire inside the capillary and gluing it with epoxy in order to apply the high voltage at the exit of the capillary.

Microfluidic devices are composed of a plate or a film with covered microchannel networks and are principally developed for electrophoretic separations. These systems are coupled to a mass spectrometer in an ever-growing number of cases. Such a coupling is ensured by a nanospray interface, which is able to work with a slow flow rate (typically 1 to 500 nL/min). Several approaches have been shown to reach this goal, mainly glass chips being coupled to an MS through a liquid junction (Figues et al, Analytical Chemistry, 1998 vol. 70 p 3728) or by adjusting a nano-tip at the end of the microchip (Li et al, Analytical Chemistry, 1999 vol. 71 p 3065). In an alternative system described by Ramsey et al, Analytical Chemistry, 1997, vol. 69 p 1174, the microchannel end has been directly coupled to an MS, by applying the potential from a side capillary. An interface between a polymer-based microchip in PDMS and a capillary for the nanospray coupling has also been suggested by Chan et al, Analytical Chemistry, 1999 vol. 71 p 4437. An interesting point is that this configuration allows the multiplexing of capillaries and opens the way to multiple analyses in a minimum of time. In another concept described by Xu et al, Analytical Chemistry, 1998 vol. 70 p 17, the solution is pumped through a membrane cut-off and the solution is driven to a metallized spray tip to the MS. In WO 98/35376, an electrospray nozzle has a filter structure that is integrated between the sample inlet and the channel tip outlet. The concept of multiplexing a nanospray is presented in U.S. Pat. No. 5,872,010, in which a covered microchannel array is used for feeding the mass spectrometer. The high voltage is applied in a sample or buffer reservoir and not by a conductive region inside the covered microchannels. Numerous methods have been described in which microchips have been coupled to an MS, through more or less direct interfaces.

In another format, a polycarbonate chip was fabricated by mechanically machining a cone in a polymer block, and using a laser to etch a capillary system in one of the polymer blocks that ended in an electrospray nozzle. (Wen et al. Electrophoresis 2000, 21, 191–197). This format necessitates the etching of a polymer by machining in order to remove material to form a tip shape more suited for electrospraying.

In another work, Kim et al. (Kim et al. Electrophoresis 2001, 22, 3993–3999) presented a way of fabricating arrays of electrospray in PDMS by casting that can be directly interfaced to the MS. Nevertheless, because of the fairly thick polymer they use for stability, they have to assist the flow with nitrogen in order to generate a stable spray. Otherwise, some authors (WO 00/15321) presented a way of fabricating nanospray nozzles in silicone that can be further interfaced with glass or plastic chips. Nevertheless, in this work, the authors did not mention machining a plastics chip to form the nozzle.

The integration of microelectrodes, microholes and microionodes (i.e. composite ion permeable membranes) has been achieved recently by photoablation or by plasma etching, for the electrochemical detection of electroactive or ion species as well as for decoupling two electrical fields in a capillary electrophoresis column and an electrochemical detector.

SUMMARY OF THE INVENTION

From a first aspect, the present invention provides an apparatus for dispensing a sample for subsequent analysis by mass spectrometry, comprising a polymer substrate of electrically insulating material, the substrate comprising a covered microchannel along which the sample is to be delivered, the microchannel communicating with an outlet through which the sample is to be sprayed, characterized in that a portion of the substrate, defining a portion of a wall of the microchannel, comprises an electrically or ionically conductive material for applying a voltage to the sample, said conductive portion of the substrate having a controlled size and location, for spraying the sample from the outlet by application of a voltage. Preferably, the apparatus has at least one dimension smaller than 200 µm; if said dimension is thickness then the multilayer apparatus is thin enough to avoid a large surface surrounding the outlet. WO 01/56771 discloses how to make thin film microchannel devices.

An outlet end of the apparatus may be perpendicular to the channel direction, or, may taper in the spraying direction, e.g. in a V-shape, or may be three dimensionally etched to minimize the surface exposed to drop formation.

The placement of the flow resistant conductive part (e.g. electrode, ionode, ion exchange membrane) in the wall of the covered microchannel guarantees that the sample flow is laminar without the creation of turbulences. This is important if the device is to be used as a detector for liquid chromatography or electrophoretic analysis. In an option, this conductive portion of the substrate may comprise a metallic layer, a conductive ink, or a conductive polymer such as e.g. polypyrrole, polyaniline or a conductive gel so as to be in contact with the solution to be sprayed. The high voltage is then applied through this conductive layer. The current lines are forced to cross the solution to be analyzed and therefore the ionization is very efficient and stable, reducing the risk of generating corona discharges.

In certain cases, a sensitive sample must not be directly in contact with an electrical conductor per se. In such cases, the conductive section comprises a conductive electrolyte such as an organic material, an aqueous gel or solution or any material that physically isolates the electrode from the sample while maintaining the electrical conductivity of the system. In this case again, the solution content can be modified by providing ions from the ionode, for acidification.

Preferably, the distance between the conductive portion of the microchannel and the nozzle is between 0.01 and 10 mm. An important aspect of the present invention is that the electric field in the covered microchannel is collinear with the laminar flow.

In another option, the spraying current density can be controlled using the electrode inserted in the microchannel or by an external electrode in contact with a reservoir.

The substrate and the cover are preferably formed from a hydrophobic material such as a polymer or a ceramic. The microchannel preferably has at least one dimension, preferably width, of less than 150 μm. The substrate may advantageously comprise a network of covered microchannels. The nanospray can thus be coupled to a capillary network currently called a micro total analysis system (μTAS), used for example for capillary electrophoresis, chromatography or affinity separation.

The apparatus may comprise means for applying a further voltage to a portion of the microchannel, such as a reservoir, remote from the conductive portion of the substrate.

In an embodiment of the apparatus, at least a portion of said covered microchannel is coated or filled with biological material, for example proteins, sugars, oligonucleotides or cells, in order to perform at least one biological assay such as affinity, activity, or an immunoassay.

The apparatus may also comprise a separation means, for example a solid phase (e.g. a membrane, beads or a section of the microchannel wall), a chromatography medium or a capillary electrophoresis system.

It may be convenient to locate a decoupler between a separation part of the microchannel and the outlet in order to enable partial or total electrical decoupling between the electrophoresis electric field and the spraying electric field.

From a second aspect, the present invention provides a method of dispensing a sample from an apparatus as defined above. Electric current may be used to generate a species at the conductive substrate portion. The species could comprise protons, quinones or other redox species that can further react with another species in the sample.

This method may comprise immobilizing molecules of the sample reversibly on a solid support (e.g. a membrane or beads), and releasing said molecules from the solid support into the microchannel by a spraying buffer or by a gradient of different solvents. At least one affinity agent may be immobilized on said solid support, said affinity agent being selected from antibodies, antigens, receptors, DNA strains and the like. The solid support may be placed in contact with the microchannel after the step of immobilizing the molecules of the sample, or may be integrated in the apparatus prior to use thereof. An affinity assay may be made on the solid support, said solid support being a membrane and/or beads retained by a restriction in the micro-channel. In another embodiment, said solid support is placed in a reservoir at the entrance of the microchannel. Said molecules may be transblotted to said solid support from a gel or another separation support. A chemical reaction, and/or an affinity reaction, e.g. comprising at least one of desalting, enzyme digestion, chemical digestion, chemical transformation or purification, may occur in or on said solid support prior to the releasing step. Particularly in the case of desalting, preferably the step of immobilizing said molecules comprises adsorption thereof on said solid support, and the releasing step comprises washing said solid support with an aqueous solution and desorbing said molecules of the sample to be sprayed by a different solution, said solution being composed of e.g. an organic solvent (e.g. methanol, acenonitrile) and an acidic or basic species, or combinations thereof.

The solid support may be selected from polymers, ceramics, metallic and glass materials; e.g. polyvinylidenefluoride (PVDF), nitrocellulose, cellulose acetate, acrylamide, agarose, or the like.

A separation may be performed in the microchannel prior to spraying of the sample from the outlet. An organic phase may be deposited at the inlet of the microchannel in order to avoid evaporation of the solution to be sprayed.

From a third aspect, the present invention provides a method of fabricating an apparatus for dispensing a sample for subsequent analysis by mass spectrometry, comprising the steps of taking a polymer substrate of electrically insulating material, fabricating a microchannel in the substrate by an etching process, providing an outlet through which the sample can be sprayed from the microchannel, forming a portion of the substrate, defining a portion of the covered microchannel wall, from an electrically conductive material for applying a voltage to the sample, whilst controlling the size and location of said conductive portion of the substrate, and covering the microchannel.

When the substrate is a polymer, the covered microchannel may be formed by laser photoablation, UV-Liga, embossing, injection molding, solvent casting, light or thermal induced polymerization. The conductive portion of the substrate may also be formed by the deposition of an ink, conductive polymer, ion exchange material, metal deposition, sputtering or other. Alternatively, the microchannel and/or the conductive portion may be formed by plasma etching, photoablation or chemical etching. Conductive substrate portions formed in these ways are ideal for applying a high voltage in the microchannel in order to generate a stable spray for feeding a mass spectrometer.

The conductive substrate portion may in particular be formed by making a recess in the substrate and filling the recess with electrically conductive material.

An analytical instrument comprising an array of apparatuses, each according to the invention, can be used in a method of analyzing a plurality of samples, each apparatus being used in turn to collect a sample, and each sample can be dispensed from the respective apparatus, and analyzed by mass spectrometry. Said samples may be collected from an analytical system, e.g. a chromatograph, an electrophoretic unit, a separation unit or an affinity system.

The invention will now be described in more detail, by way of example only, with reference to the accompanying drawings, in which:

DETAILED DESCRIPTION OF THE PREFERRED EMBODIMENTS

Figure 1:
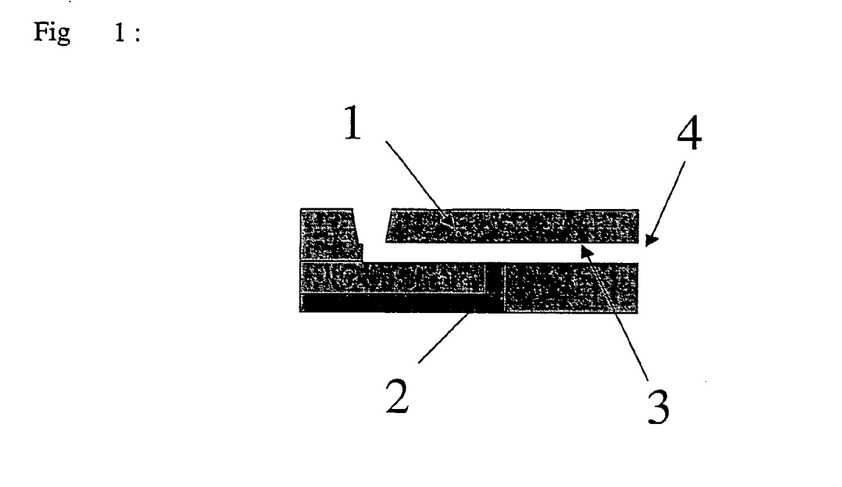
FIG. 1 is a schematic vertical section through an apparatus according to an embodiment of the invention.
Figure 2:
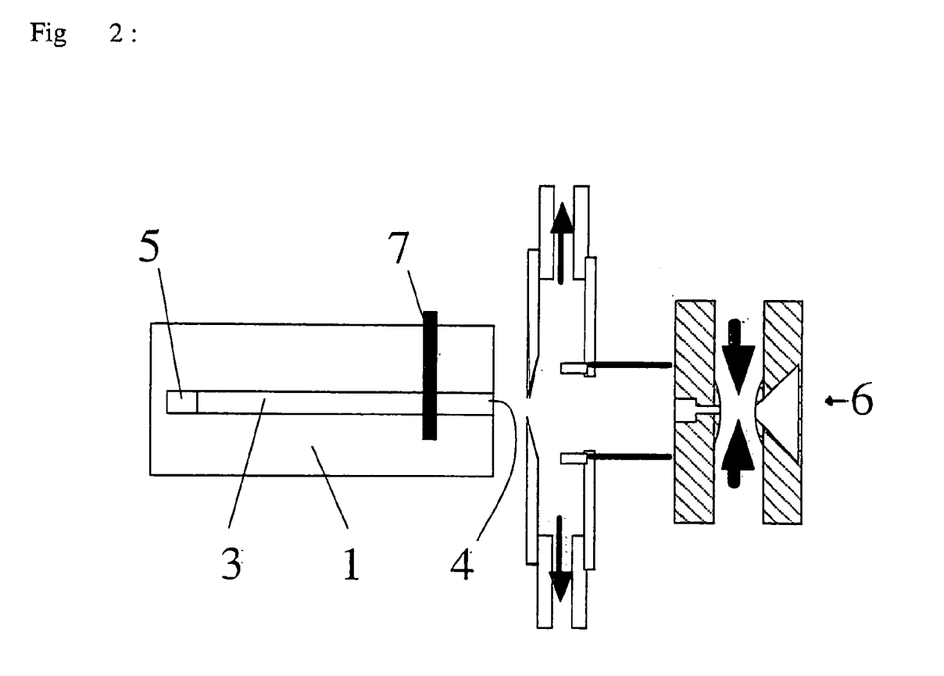
FIG. 2 schematically shows how the apparatus can be coupled to an MS entrance.

FIGS. 1 and 2 show a sample-dispensing apparatus according to an embodiment of the invention comprising a microchip substrate 1 formed from e.g. polyethylene terephthalate (PET). In manufacturing the apparatus, a recess in the form of a microchannel of 55×200 μm (cross section) is firstly photoablated in the polymer foil. This 5-cm line is then filled with an electrically conductive material, in particular a carbon ink 2 (Electra, Electrador, UK). The microchip 1 is then inverted and a new microchannel 3 of 50×20 μm is photoablated on the other side from, and perpendicularly to, the carbon filled microchannel 2. This results in a microelectrode of 20×200 μm appearing at the bottom of the microchannel 3. The microchannel 3 is then covered by lamination and an outlet 4 is laser cut at a distance of 1 cm from the carbon ink electrode, so that this extremity of the microchannel 3 appears on the side of the polymer foil. The outlet 4 is etched in such a way that the external width of the microchannel end is less than 30 μm and hydrophobic, avoiding wetting of the surface of the microchip by the sample solution. The microchannel has an inlet 5 from the top of the microchip.

The structure is then placed in a flow cell connected to a syringe pump and placed before the entrance of the mass spectrometer 6 as shown in FIG. 2. A solution is forced by backpressure (10 to 2000 nL/min) and a positive potential is applied throughout the carbon line for the ionization.

Figure 3:
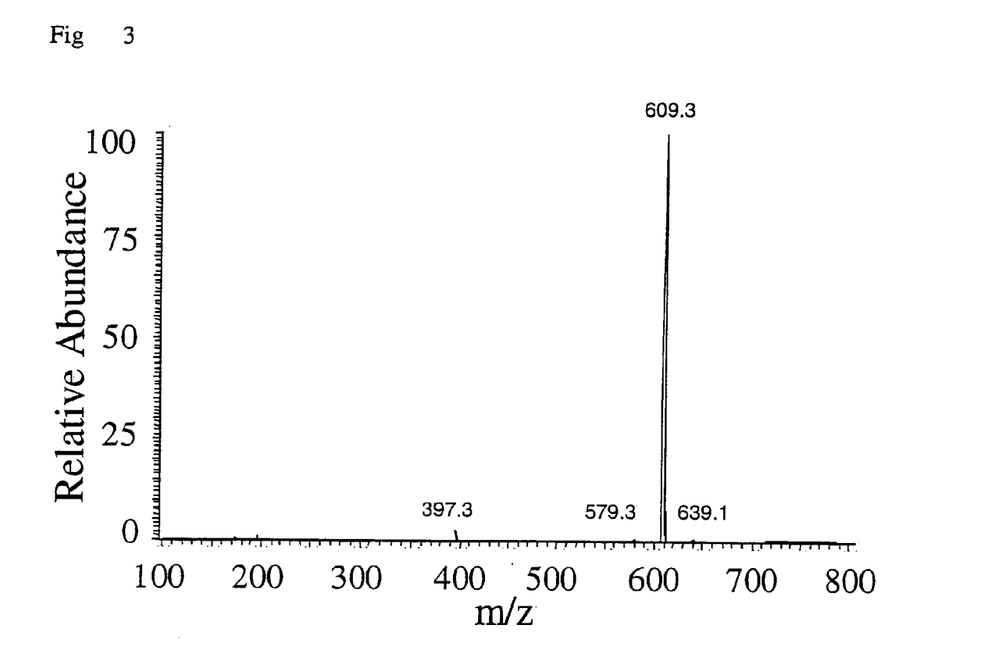
FIG. 3 is a mass spectrum obtained using the apparatus according to FIG. 1 to analyze reserpine.

The results presented in FIG. 3 show the detection of 1 mg/mL reserpine at a flow rate of 200 nL/min under a polarization of 5 kV. This spectrum was obtained with an Ion Trap LCQ duo Mass Spectrometer (Finnigan, US).

An analysis of the spectrum shows the soft ionization procedure that has been possible with this structure. The fragmentation of the molecule is at a minimum and the mass peak exactly corresponds to that obtained with a standard sheath electrospray interface.

Figure 4:
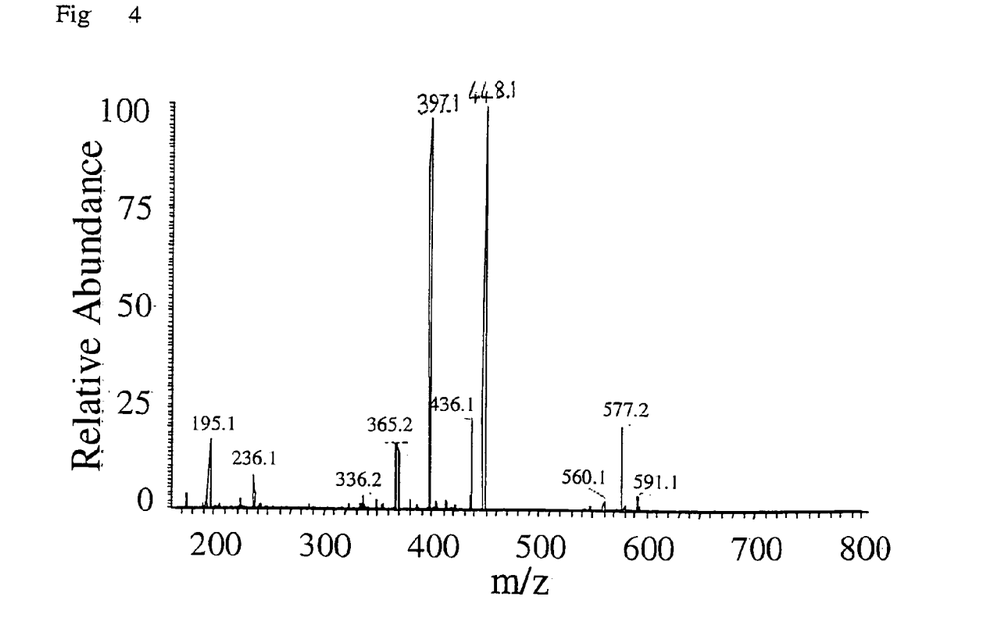
FIG. 4 is a tandem mass spectrometry analysis of the parent ion 609.3 corresponding to the molecular weight [M–H+] of reserpine.

FIG. 4 shows a simultaneous MS—MS analysis which was also performed in order to analyze the fragment of the parent ion 609.3 corresponding to the molecular weight [M–H+] of reserpine. The different peaks correspond to the expected fragments and the total spectrum could be resolved.

Figure 5:
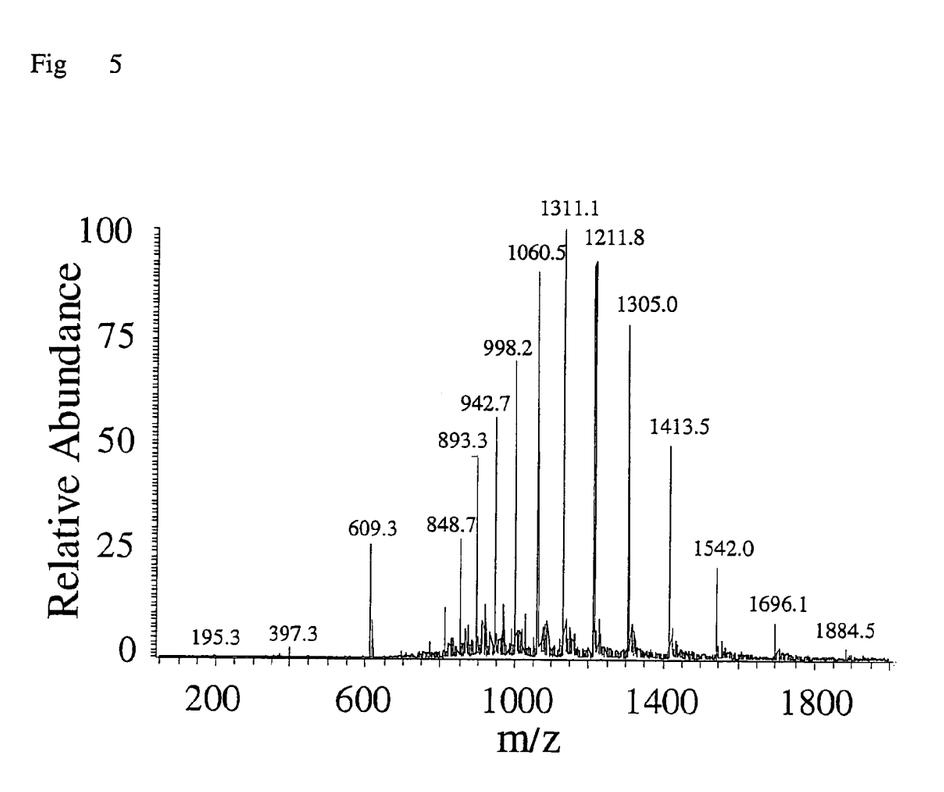
FIG. 5 is a mass spectrum obtained using an apparatus according to FIG. 1 to analyze myoglobine and reserpine.
Figure 6:
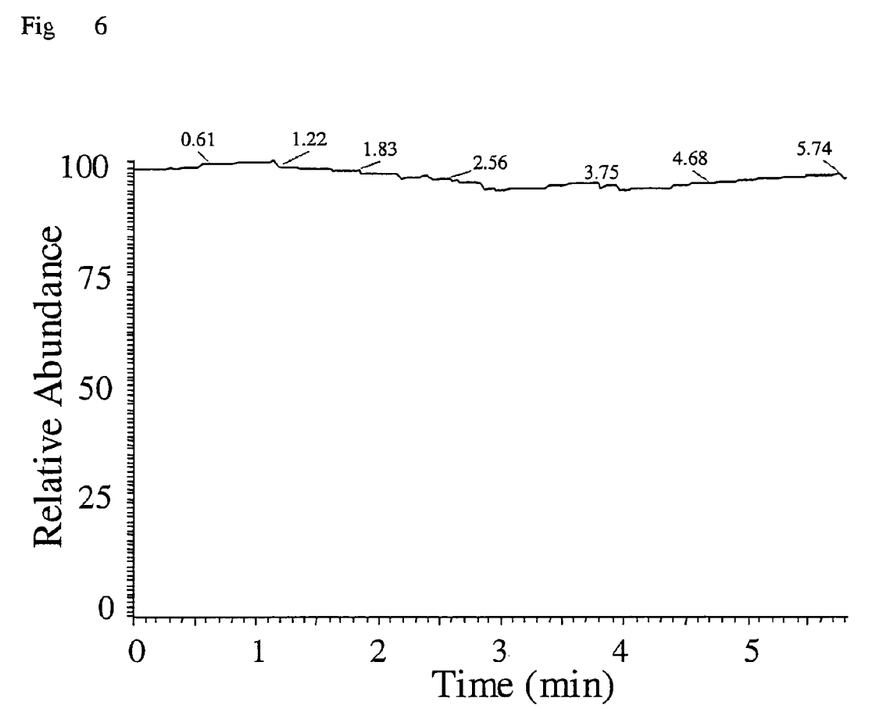
FIG. 6 shows the intensity of the detection of the results shown in FIG. 5.

The present system can be used for the analysis of protein as exemplified with the following experiment: 25 μM of myoglobin were pumped through the device and sprayed again with the same procedure as that described with respect to FIG. 3. The results are given in FIG. 5 and show the peaks of protonated myoglobine. Each peak represents a different charge on the protein, between 9 and 22 times positive. The intensity obtained here demonstrates the accuracy of the technology. Another very important characteristic of a nanospray is its stability during a long analysis time. Results taken over several minutes and shown in FIG. 6 demonstrate that over such a period the signal is still maintained between 95 and 100%. This proves that the degradation of the nanospray is not critical, as it could be if the spray was fabricated in glass and derivitized with a hydrophobic layer at the capillary end.

Depending on the solution to be analyzed, the application of the voltage within the microchannel can provide or consume protons and therefore change the pH of the solution. This fact can be used in order to acidify a protein sample for example at the end of a separation before sending it to the mass spectrometer. As the electrode has defined position and size inside the microchannel, the current density generated at the electrode is directly correlated to the change in pH inside the microchannel. This effect is a consequence of the oxidation of water that occurs during the spraying of the solution:

$$2H_2O - 4e^- \rightarrow 4H^+ + O_2 \qquad \text{Equation 1}$$

From equation 1, it is obvious that the concentration of protons will be proportional to the current. However, this is only true if the protons produced are localized in a defined volume such as in the microchannel. In known electrospray ionization techniques in which the electrode is outside the capillary in the sheath liquid, the protons produced are not distributed in a controlled manner with respect to the analyte solution. In known systems using a wire inside the capillary, such as the system described in U.S. Pat. No. 5,872,010, the size of the electrode so formed is not controlled and therefore the current density at the electrode is not controlled either. Furthermore, the presence of a metallic wire or other protruding electrode inside the capillary provides turbulences to the flow, reducing the resolution of the capillary electrophoresis separation. In both types of known systems, therefore, control of the reaction defined by equation 1 is difficult. By contrast, in the present invention, the position and size of the electrode are precisely defined, and the electrochemical acidification can therefore be accurately controlled.

Figure 7:
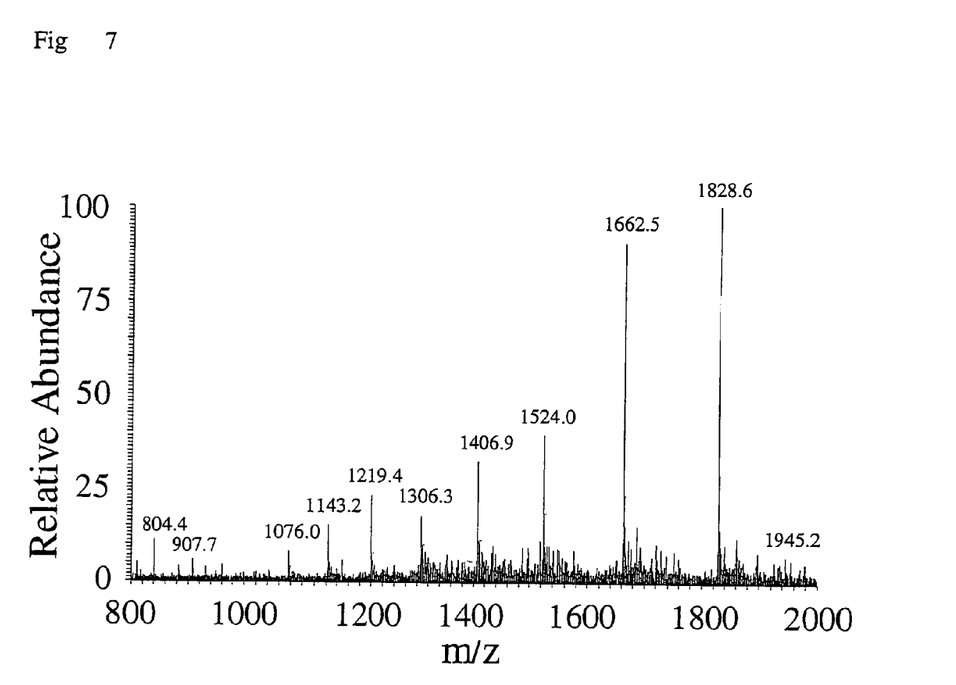
FIGS. 7 and 8 are mass spectra for a solution of β-lactoglobulin B taken at different spray currents.
Figure 8:
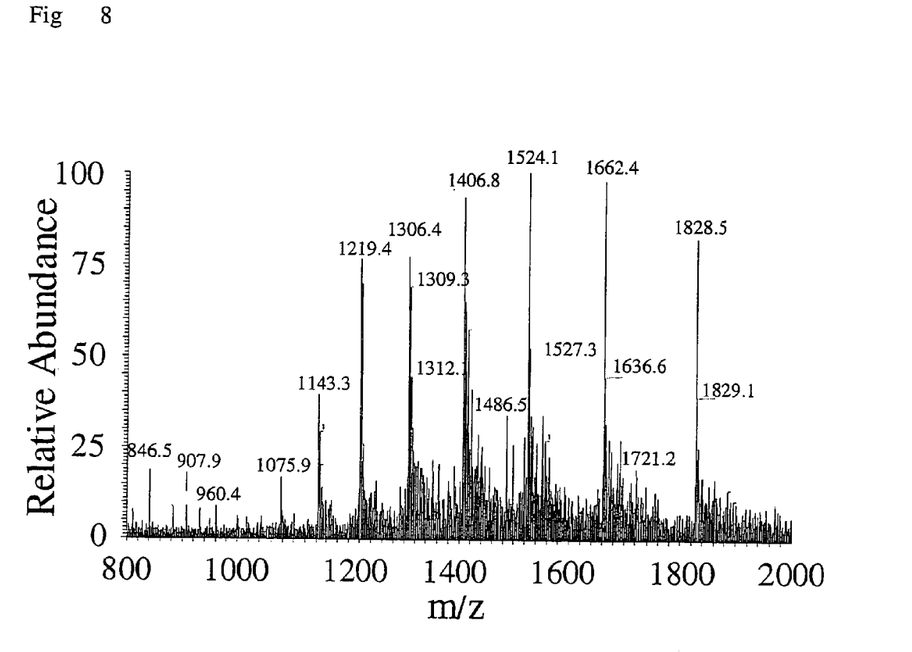

To illustrate such control, FIG. 7 shows a mass spectrum of a 3 µM solution of β-lactoglobulin B from bovine milk in 50/49/1 (v/v/v) $CH_3OH/H_2O/CH_3COOH$. The solution was sprayed at approximately 200 nL/min with a spray current of 100 nA. FIG. 8 shows a mass spectrum of an identical solution taken under the same conditions except that the spray current was 150 nA. It is immediately apparent that the peaks seen in FIG. 7 have been shifted to the left in FIG. 8, meaning that the protein is more highly charged. This is due to the production of a greater concentration of protons at the electrode, which brings about a decrease in pH.

Figure 9:
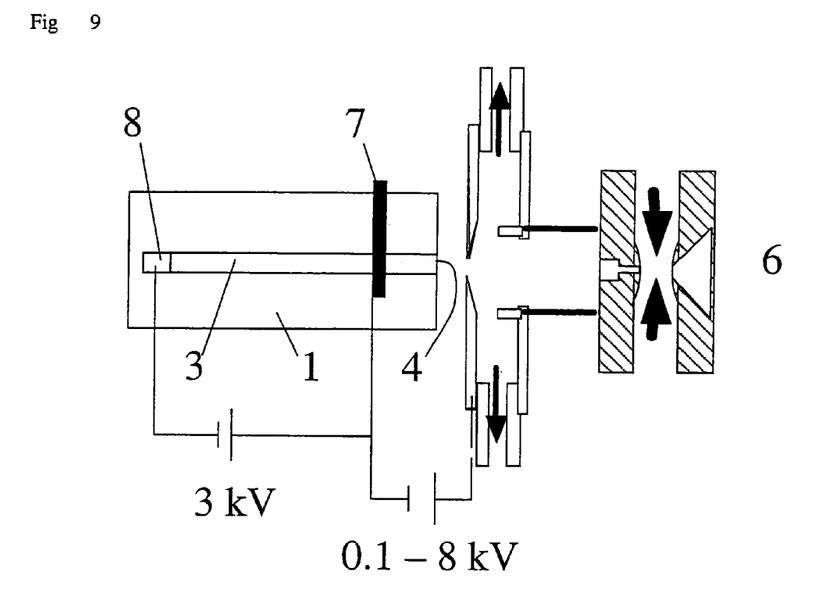
FIG. 9 is a schematic diagram of apparatus according to an embodiment of the invention using electroosomotic flow.
Figure 10:
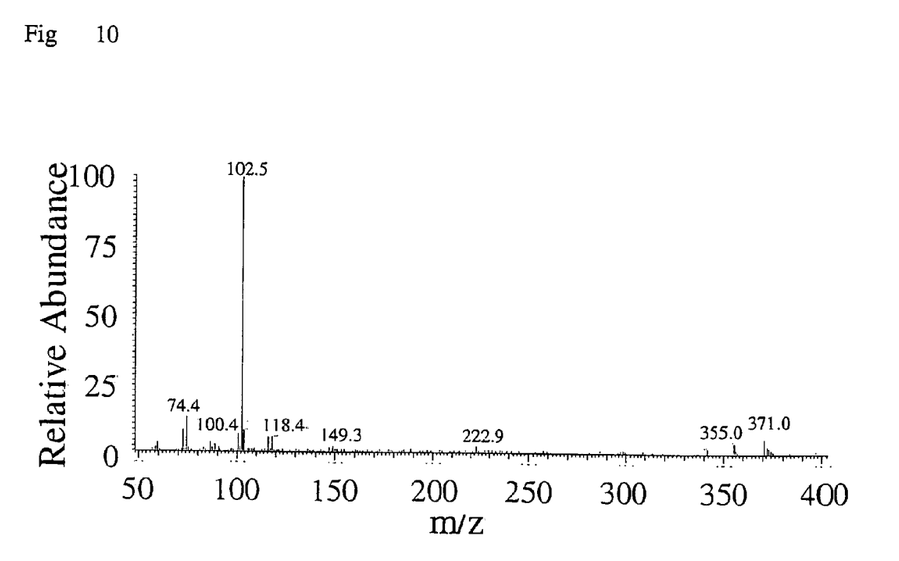
FIG. 10 is a mass spectrum of a solution of tetraethyl ammonium (TEA) obtained using the apparatus shown in FIG. 9.

The presence of the electrode inside the microchannel allows the spraying to take place at a constant voltage even if another voltage is applied to the apparatus for the purpose of separation. For example, FIG. 9 shows a ionization microelectrode 7 polarized at 7 kV vs. the mass spectrometer 6, grounded at 0 V. Despite its high voltage, the microelectrode 7 serves as a cathode for an additional non-grounded electrical circuit. In the example shown, a floating voltage of 3 kV is applied between a reservoir 8, formed at the inlet to the microchannel 3, and the microelectrode 7. This floating voltage of 3 kV is used for electrophoretic separation of the analyte and also for electroosmotic pumping thereof. FIG. 10 shows a mass spectrum of a 5 mM tetraethyl ammonium (M 102.8) buffered at pH 8 obtained using the apparatus shown in FIG. 9.

In an alternative configuration, a voltage of 7 kV is applied to the electrode 7 and a separate voltage of 11 kV is applied to the reservoir 8 to achieve the same result. Both alternatives confer the significant advantage of always having controlled separation and spray voltages and currents during the analysis.

Biochemical and/or biological assays require a fine analysis of the activity of the molecule and for instance the affinity between this molecule and an antibody or a receptor. For such applications, it can be advantageous to perform the assay detection by mass spectrometry since this allows direct recognition of the molecule of interest. To this end, arrays of apparatuses according to the invention can be coated with antibodies and exposed to the sample solution. An antigen in solution can then be captured from the antibody, washed with a buffer solution and exposed to an acidic solution to release the antigen into solution; the microchannel array is then exposed in front of the mass spectrometer entrance. By applying a high voltage in individually addressable electrodes in contact with the solution and optionally applying a pressure, the protonated antigens can be sprayed into the mass spectrometer from each individual apparatus of the assay.

Figure 11:
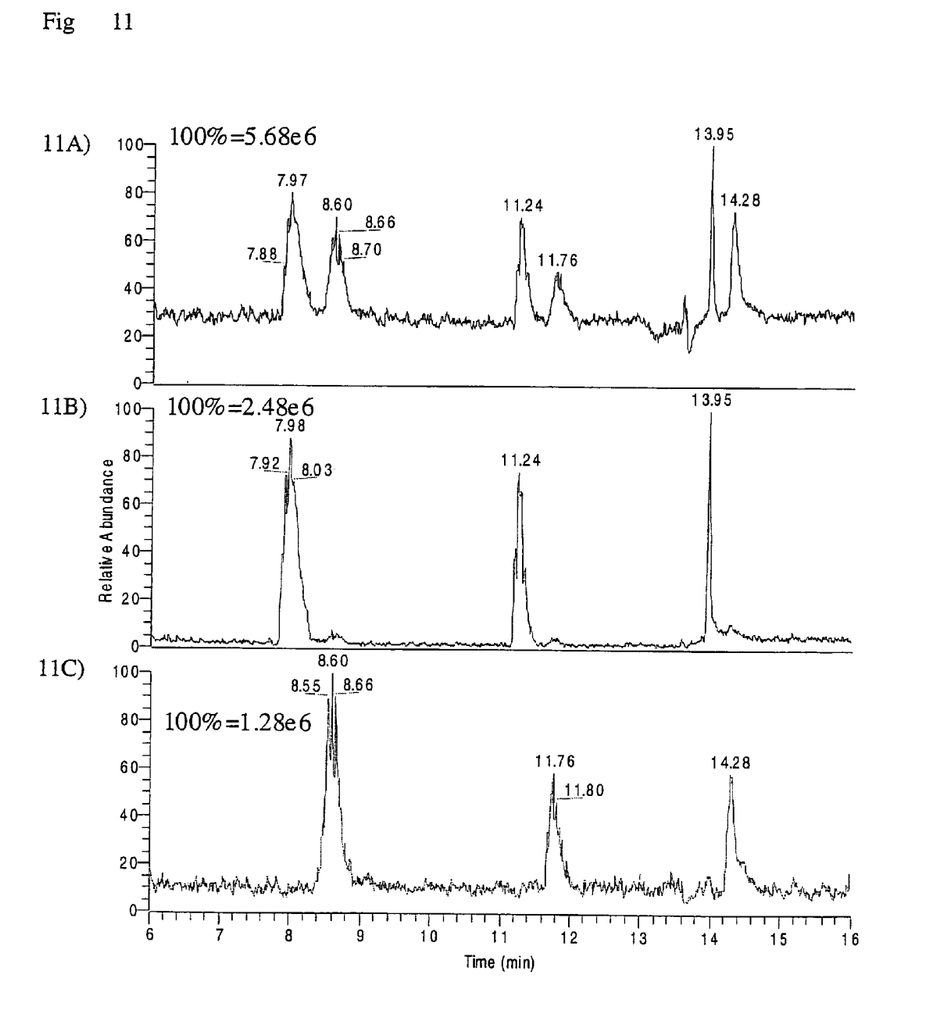
FIGS. 11A to 11C are electropherograms showing the time evolution of: A) the entire detected signal; B) the signal obtained at the mass corresponding to the tetramethyl ammonium ion; and C) the signal obtained at the mass corresponding to the tetraethyl ammonium ion; of a solution of 1 mM tetramethyl ammonium+100 mM tetraethylammonium in 50% methanol:water buffered at pH 7 with 10 mM ammonium acetate obtained using apparatus similar to that of FIG. 9.

Separation of compounds in the apparatus can be performed before the sampling in the mass spectrometer as shown in FIG. 11, capillary electrophoresis being performed on the chip before a sample is sent to the MS. A most important point is that the thickness of the full apparatus was less than 200 µM; in the present example, the thickness of the apparatus was 85 µm. In this case, the chip was fabricated by plasma etching in a polyimide substrate of 50 µm in thickness. A channel of 100×30 µm, and 11 cm long, was fabricated with a cross injector at one extremity, the cross injector comprising two side arms of 1 cm each in length in order to introduce the sample solution. The other extremity was formed similar to that shown in FIG. 9. The substrate was then laminated with a 35 µm thick laminate.

FIG. 11 shows examples of electropherograms obtained for the separation of tetramethyl ammonium and tetraethyl ammonium ions by capillary electrophoresis performed in this apparatus. Repetitive injections, separations and on-line mass spectrometry analyses were performed continuously. In particular, FIG. 11A shows the electropherogram obtained with a Ion-Trap LCQ Duo mass spectrometer (Finnigan, US) for a mixture of 1 mM tetramethyl ammonium+100 mM tetraethyl ammonium which is injected three times into the separation channel, and electrophoretically separated upon application of 6 kV, the injection duration being 9 seconds from a side reservoir, before being sprayed into the mass spectrometer by application of the same voltage. The solution used here was a 50% methanol:water mixture buffered at pH 7 with 10 mM ammonium acetate, and the electropherogram shows the total signal recorded by the mass spectrometer as a function of time. FIGS. 11B and 11C show the time evolution of the detected signal at the mass corresponding to the single ions, namely to tetramethyl ammonium and tetraethyl ammonium, respectively. Comparison between these three electropherograms clearly show that tetramethyl ammonium has a smaller retention time than tetraethyl ammonium.

Figure 12A:
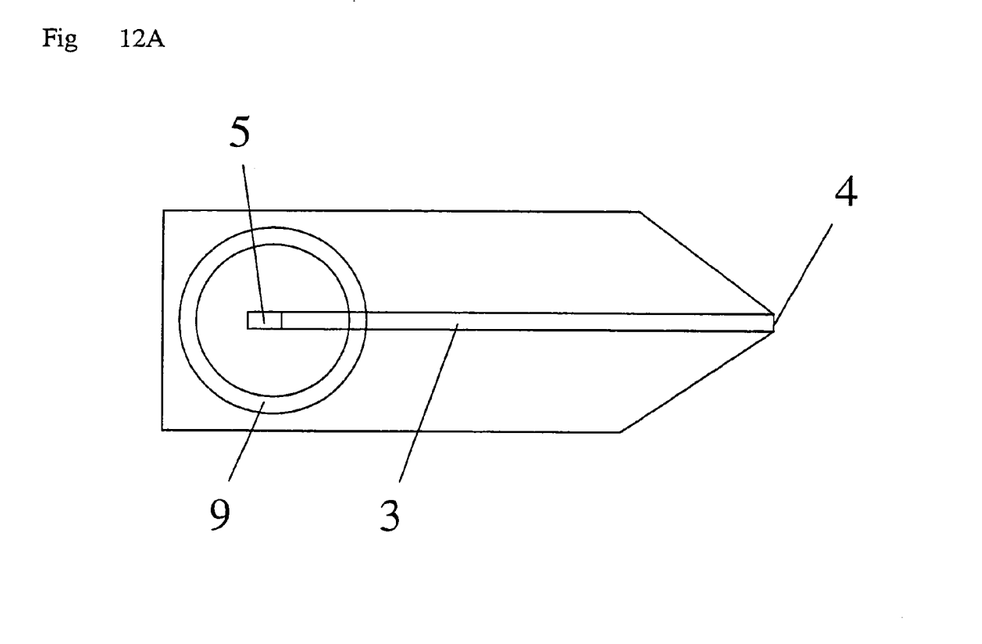
FIGS. 12A and 12B are a schematic top view and a schematic section respectively of apparatus for dispensing a sample wherein a reservoir surrounds the microchannel entrance.
Figure 12B:
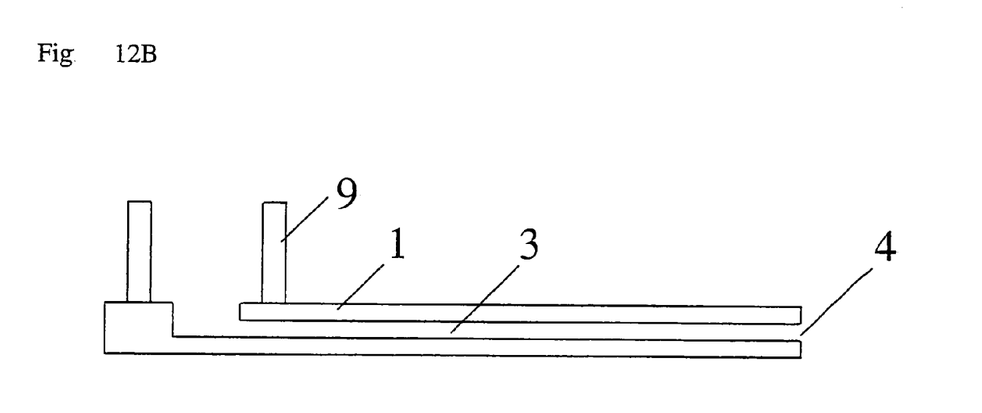
Figure 13A:
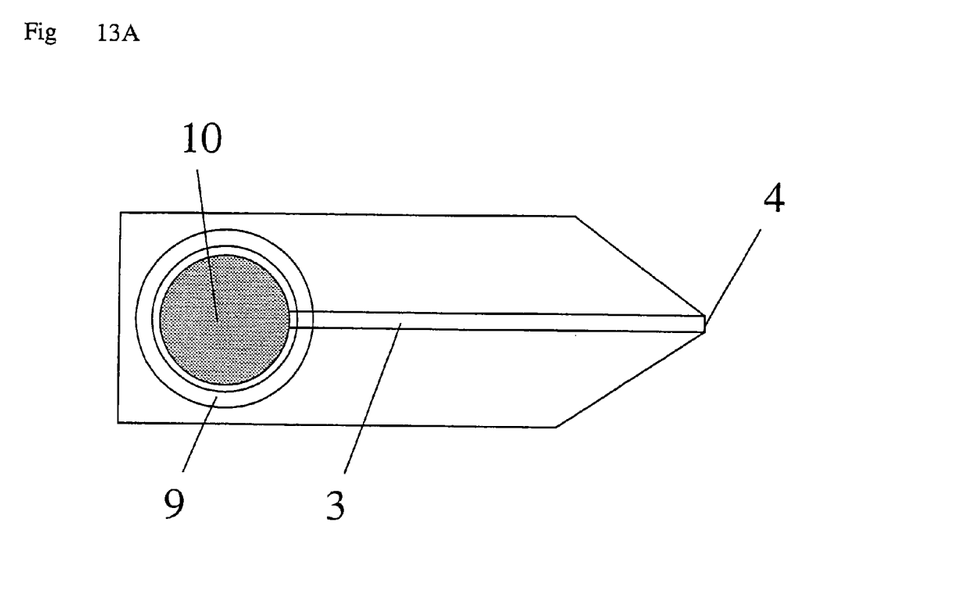
FIGS. 13A and 13B are a schematic top view and a schematic section respectively of a variant of the apparatus of FIGS. 12A and 12B.
Figure 13B:
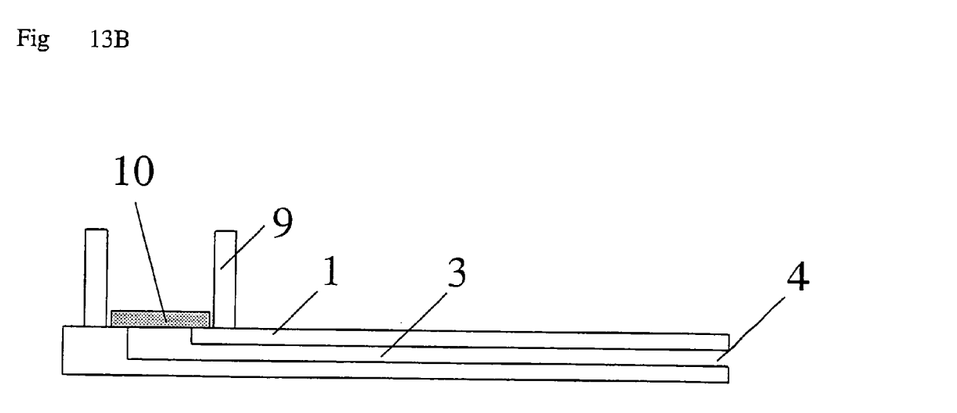
Figure 13C:
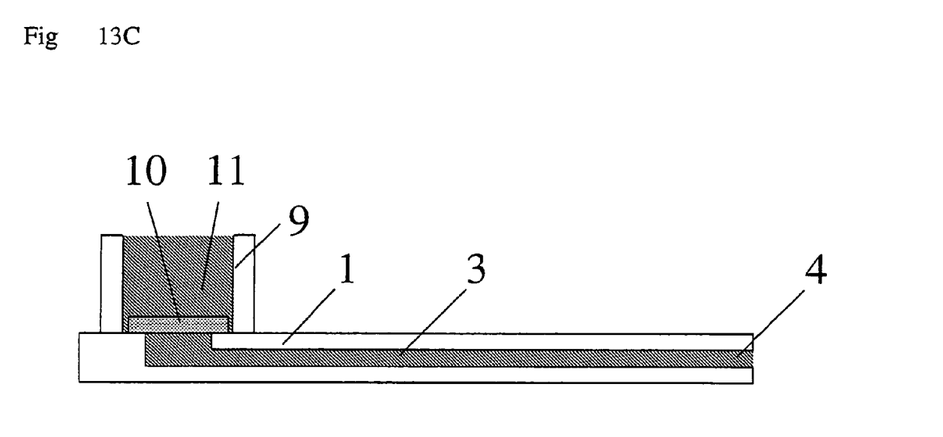
FIG. 13C shows the variant apparatus of FIGS. 13A and 13B with a desorption solution added thereto.
Figure 13D:
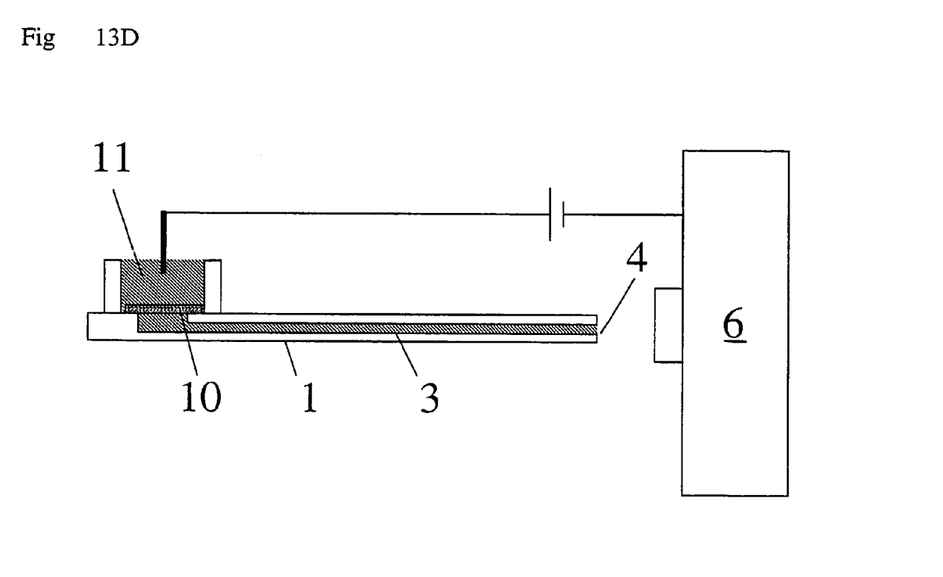
FIG. 13D shows the application of a voltage to the reservoir of the variant apparatus.

FIGS. 12A and 12B show an apparatus fabricated by laser ablation and/or plasma etching. A solution can be placed in the reservoir 5 and the voltage is applied either by the integrated electrode or by an external electrode (neither shown) to spray the solution through the open end 4 to the mass spectrometer. It is again important to distinguish that the thickness of the device should be smaller than 200 µM, and therefore that the system is fabricated with plastic films. The sampling can be achieved without sheath liquid and without assistance of an induced flow. Indeed, if the parameters of hydrophobicity, thickness and electric field and shape are optimal, the spray can be generated without sheath gas, sheath liquid or pressure. A chamber 9 can also be placed in contact with the reservoir in order to store the solution to be sprayed.

In another embodiment, a purification step such as immunocapture or desalting can be performed prior to spraying a sample as shown in FIG. 13. A solid support in the form of a membrane 10 is placed in the chamber 9, and a sample is added to said chamber, so that molecules adsorb on said membrane 10. Washing steps are performed to remove non-adsorbed species on said membrane. As shown in FIG. 13C, a desorption solution 11 is then introduced to desorb the molecules, which are finally sprayed to the MS by applying a voltage to the reservoir as shown in FIG. 13D.

In order to demonstrate this concept, an experiment has been conducted with angiotensine II. A solution of 0.1 mg/ml of anti-angiotensine was prepared and placed in contact with a 8 mm diameter polyvinylidenefluoride (PVDF) membrane 10 for 15 min undergoing shaking. The membrane 10 was then washed with water and placed in the chamber 9 in contact with the entrance of the microchannel. 50 µL of spraying buffer (50% MeOH/49% Water/1% Acetic Acid) were then added to the chamber 9 and an electrical contact applied 1.8 kV to the chamber.

Figure 14A:
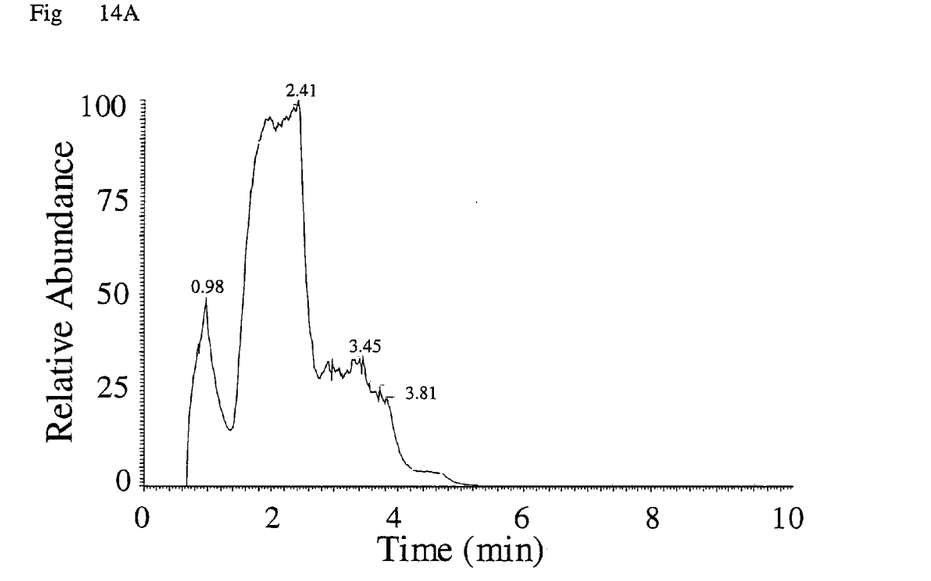
FIGS. 14A and 14B show mass spectrometry results for the detection of an angiotensine solution obtained using the apparatus of FIGS. 13A and 13B.

FIG. 14 shows the mass spectrometry results of this experiment whereby angiotensine, specifically captured by adsorbtion on the PVDF membrane 10 containing anti-angiotensine as mentioned above, was then sprayed into the MS with the membrane modified chip. Upon application of the voltage, the spraying buffer was electrokinetically pumped through the microchannel of the apparatus and sprayed into the mass spectrometer. As shown in FIG. 14A, the intensity of the signal increases from background noise to a very intense signal due to the desorption of the angiotensine from the membrane 10. After a few seconds, the intensity decreases because the desorbed molecules have all been sprayed into the MS. This highlights the fact that when the desorption occurs in the chamber, the molecule of interest is not diluted therein but very rapidly transported to the MS, because the membrane is in contact with the microchannel entrance, in which only laminar flow occurs and in which mixing is minimized by avoiding the presence of protruding features creating obstacles to the flow of solution.

Figure 14B:
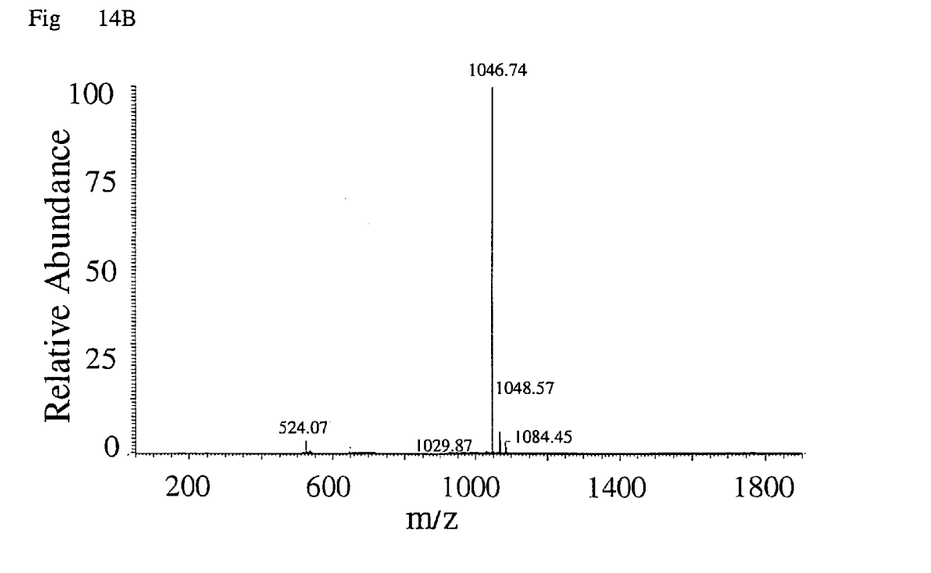

FIG. 14B shows the mass spectrum obtained after 1.87 minutes of injection into the mass spectrometer, confirming that angiotensine is the detected molecule.

In another experiment, the membrane 10 is integrated to the spraying device and adsorption, washing and release steps are performed by passing the successive solutions in the device by aspiration from the open end 4 prior to spraying the solution into the MS.

In another example, anti-angiotensine antibody is first immobilized on the membrane to capture angiotensine specifically. It is difficult here to distinguish between specific (antibody-antigen) and non specific (physisorption) adsorption signal. However, different membranes preventing the non-specific adsorption such as polyethylene glycol or sugar based material can be used to reduce this non specific adsorption. In another case, the surface may be blocked by bovine serum albumine or other blocking agent, either by non-reversible adsorption or covalent attachment.

In alternative embodiments of the invention, a solid support such as the membrane 10 and/or beads could be added to the apparatuses shown in FIG. 1, 2 or 9 or the apparatus described above with respect to FIG. 11.

It must be added that many of the concepts presented above have been realized and that they can be multiplexed and automated. The different pieces can optionally be placed in a network of capillaries where the solution is driven either by pressure with a syringe or a pump or by electroosmosis.

The invention claimed is:

1. An apparatus for dispensing a sample for subsequent analysis by mass spectrometry, comprising a polymer substrate of electrically insulating material, the substrate comprising a covered microchannel along which the sample is to be delivered, the microchannel communicating with an outlet through which the sample is to be sprayed, characterized in that a portion of the substrate, defining a portion of a wall of the microchannel, comprises an electrode for applying a voltage to the sample, said electrode having a controlled size and a controlled location inside the microchannel, for spraying the sample from the outlet by application of a voltage.

2. An apparatus according to claim 1, having a thickness smaller than 200 μm.

3. An apparatus according to claim 1, wherein the electrode comprises an electrically conductive ink or a metallic layer.

4. An apparatus according to claim 1, wherein the electrode comprises at least one of a conducting polymer, polypyrrole, and polyaniline.

5. An apparatus according to claim 1, wherein the electrode comprises a conductive gel or an ion exchange polymer arranged to be in contact with the sample to be sprayed.

6. An apparatus according to claim 1, wherein the distance between the electrode incorporated in the portion of the wall of the microchannel and the outlet is between 0.01 and 10 mm.

7. An apparatus according to claim 1, wherein the microchannel has at least one dimension of less than about 150 μm.

8. An apparatus according to claim 1, wherein the substrate comprises a network of microchannels.

9. An apparatus according to claim 1, further comprising means for applying a further voltage to a portion of the covered microchannel remote from the electrode incorporated in the portion of the wall of the microchannel.

10. An apparatus according to claim 1, wherein an outlet end of the apparatus tapers in the spraying direction.

11. An apparatus according to claim 1, in which at least a portion of said covered microchannel is coated or filled with biological material, in order to perform at least one biological assay including one of an affinity, activity, and an immunoassay.

12. An apparatus according to claim 11, wherein the biological material is selected from the group consisting of proteins, sugars, oligonucleotides and cells.

13. An apparatus according to claim 1, further comprising a separation means, comprising at least one of a solid phase, a chromatography medium and a capillary electrophoresis system.

14. An apparatus according to claim 13, wherein said separation means comprises a solid phase selected from a membrane, beads and/or a section of the microchannel wall.

15. An apparatus according to claim 13, wherein a decoupler is located between a separation part of the microchannel and the outlet.

16. An apparatus according to claim 1, further comprising a reservoir connected to an inlet of the covered microchannel and an electrode in the reservoir for applying a voltage from outside the microchannel.

17. An apparatus according to claim 1, further comprising a solid support on which molecules are reversibly immobilized, and from which molecules can be released into the microchannel by one of a spraying buffer and a gradient of different solvents.

18. An apparatus according to claim 17, wherein said solid support is a membrane or beads retained by a restriction in the microchannel.

19. An apparatus according to claim 17, wherein said solid support comprises molecules that have been transblotted from a gel or another separation support.

20. An apparatus according to claim 17, wherein said solid support is made of a material selected from a group consisting of polymers, ceramics, metallic, glass materials, polyvinylidenefluoride (PVDF), nitrocellulose, cellulose acetate, acrylamide and agarose.

21. An apparatus according to claim 1, wherein the microchannel is a channel formed by laser photoablation.

22. An apparatus according to claim 1, wherein the microchannel is a channel formed by plasma etching or chemical etching.

23. An apparatus according to claim 1, wherein the electrode in a wall of the microchannel is formed by laser photoablation.

24. An apparatus according to claim 1, wherein the electrode in a wall of the microchannel is formed by plasma etching or chemical etching.

25. An apparatus according to claim 1, wherein a plurality of microchannels are fabricated in the same polymer substrate.

26. An apparatus according to claim 1, wherein the electrode is made of an electrically conductive material and is formed in a recess in the substrate.

27. An apparatus according to claim 1, further comprising a second electrode in the wall of the microchannel for applying a potential voltage, different from the voltage applied to generate the spray.

28. An analytical instrument comprising an array of apparatuses, each apparatus comprising a polymer substrate of electrically insulating material, the substrate comprising a covered microchannel along which the sample is to be delivered, the microchannel communicating with an outlet through which the sample is to be sprayed, characterized in that a portion of the substrate, defining a portion of a wall of the microchannel, comprises an electrode for applying a voltage to the sample, said electrode having a controlled size and location inside the microchannel, for spraying the sample from the outlet by application of a voltage.

29. An apparatus for dispensing a sample for subsequent analysis by mass spectrometry, comprising:
 a polymer substrate of electrically insulating material having a covered microchannel extending therein along which the sample is to be delivered, said microchannel having an outlet through which the sample is to be sprayed; and
 an electrode for applying a voltage to the sample for spraying the sample from said outlet, said electrode extending internally of said substrate such that said electrode defines a portion of a wall of said microchannel at a location within said substrate a spaced distance from said outlet.

* * * * *